United States Patent [19]

Ercoli et al.

[11] 3,998,701

[45] Dec. 21, 1976

[54] PROCESS FOR THE PREPARATION OF 17-ACYL ESTERS OF 17α, 21-DIHYDROXYSTEROIDS OF THE PREGNANE SERIES AND NOVEL PRODUCTS

[75] Inventors: Alberto Ercoli, Milan; Marco Da Col, Bologna, both of Italy

[73] Assignee: Lark S.p.A., Milan, Italy

[22] Filed: Dec. 3, 1974

[21] Appl. No.: 529,134

[30] Foreign Application Priority Data

Jan. 4, 1974 Italy ............................ 19058/74

[52] U.S. Cl. .................... 195/51 S; 260/397.45
[51] Int. Cl.[2] ................................. C12D 13/02
[58] Field of Search .................. 195/51 R, 51 S

[56] References Cited

UNITED STATES PATENTS

| 3,455,968 | 7/1969 | Herzog et al. | 195/51 R |
| 3,784,603 | 1/1974 | Shapiro et al. | 195/51 R |

*Primary Examiner*—Alvin E. Tanenholtz
*Attorney, Agent, or Firm*—Stevens, Davis, Miller & Mosher

[57] ABSTRACT

A process is disclosed for making 17-monoesters of 17 α, 21-dihydroxy steroids by acylating a 17 α, 21-dihydroxy steroid phosphate and then subjecting the intermediate 17-acyloxy-21-phosphate to dephosphorylation using an acid phosphatase to achieve enzymatic hydrolysis. Several new 17-monoesters having an anti-inflammatory property are also disclosed.

16 Claims, No Drawings

PROCESS FOR THE PREPARATION OF 17-ACYL ESTERS OF 17α, 21-DIHYDROXYSTEROIDS OF THE PREGNANE SERIES AND NOVEL PRODUCTS

The present invention relates to a new process for the preparation of 17-monoesters of 17α,21-dihydroxy steroids of the pregnane series, based on a simple reaction sequence and to products obtained from said process.

It is well known from the literature, that the 17-monoesters of 17α,21-dihydroxy steroids cannot be obtained by direct esterification of the parent diols. As a matter of fact, since the 21-hydroxy group is more reactive than the 17-hydroxy group, under sufficiently mild reaction conditions the 21-monoester rather than the 17-monoester will be formed.

Therefore, other methods have been reported to form the 17-monoesters. For instance, in British Patent Specification Nos. 1,047,519 and 1,047,518, there is described a process consisting first of the preparation of 17α,21-diesters and then of the partial saponification which takes place mainly at the expense of the 21-ester, the more reactive one, resulting in the formation of the 17-monoester.

This procedure has shown to be unsatisfactory for several reasons, the first being the difficulties which occur during the preparation of these 17,21-diesters, which are obtained, as will be explained infra in greater detail only by working under such vigorous conditions so that undesired reactions occur. If for example the steroid, in addition to the hydroxy groups in the 17α and 21 positions, also contains a third hydroxy group at C-11, this will also undergo esterification being just as, if not more, reactive than the tertiary hydroxy group at C-17. Therefore, by acylating an 11β,17α,21-trihydroxy steroid, no 17,21-diester is obtained, but rather an 11,17,21-triester which is useless for the further preparation of the 17-monoester.

The presence of a hydroxy group in position 11 compels one to carry out additional reactions which comprise initially acylating at the 21 position, then blocking the 11β-hydroxy group by forming a labile easily hydrolyzable ester, such as for example the 11-trifluoro acetate, as shown in British Patent Specification No. 1,097,164 or a labile ether, such as 11-trimethylsilyl derivative, as shown in British Patent Specification No. 1,227,992 and finally acylating the 17α-hydroxyl-group. This sequence of reactions is intended to form a mixed 11β,17α,21-triester as an intermediate, which, under gradual hydrolysis, or alcoholysis can be transformed first into a 17,21-diacyl ester and then into a 17-monoester.

It is moreover to be noted that the conversion of a 17,21-diester into a 17-monoester is not an easy process presenting technical problems of a certain difficulty. As a matter of fact a partial alkaline hydrolysis cannot be performed because of the well known migration of acyl groups from the 17α to the 21-hydroxyl group in an alkaline medium. With regard to acid hydrolysis, in the case of a 17α,21-diacyloxy steroid, hydrolysis does not lead to a single compound, but rather a mixture of several compounds, because the 21-monoester and the free 17α,21-diol are formed in addition to the 17-monoester. For this reason the recovery of the 17-monoester from this reaction mixture is very difficult.

In summary, the literature methods for the transformation of the 17α,21-dihydroxy steroids into the corresponding 17-monoester through the intermediate 17,21-diacyl derivatives are difficult because they require quite a number of steps and they are not satisfactory because of very low overall yields.

We have now found that the 17-monoesters can be obtained in a more simple way and by using only two steps — directly acylating 17α,21-dihydroxy steroid 21-phosphates and removing the phosphate group by enzymatic hydrolysis under appropriate acidic conditions.

This method object of the present invention requires therefore the use of the 17α,21-dihydroxy steroid 21-phosphate as starting material and involves the direct acylation of the 17α-hydroxy group and the successive enzymatic hydrolysis of the intermediate 17-acyloxy-21-phosphate, under controlled acidic conditions to cause splitting of the phosphoric acid residue in position 21 and the consequent formation of the 17-monoester.

As starting material any 17α,21-dihydroxy steroid-21-phosphate may be used, since the process of the present invention has general applicability.

17α,21-Dihydroxy-steroid-21-phosphates may also be called, more correctly, 17α,21-dihydroxy-steroid-21-dihydrogen phosphates, therefore both definitions used throughout the text are to be considered equivalent.

One of the remarkable advantages of the present invention resides in the fact that the 17α,21-dihydroxy steroid 21-phosphates can be acylated in position 17 under quite mild conditions, with a practically complete formation of the 17-acyl ester and without involving acylation of other hydroxyl groups if present in the molecule.

Another advantage of the process of the present invention resides in the fact that the phosphoric acid residue at C-21, in the 17-acyl ester 21-phosphates can be removed in a selective manner by an acid hydrolysis performed by means of enzymes having phosphatase properties, thus reducing the undesired reactions to a minimum.

The corticosteroid 21-phosphates used as starting materials in the process, according to the present invention, are easily available compounds which may be prepared in various ways, for example, according to known phosphorylation methods of the 21-hydroxy steroids.

The first step of the process of this invention comprises the acylation of 17α-hydroxy steroid 21-phosphates in order to achieve the direct esterification of the 17α-hydroxy-group.

As is well known to those skilled in the art, the esterification of steroids of the 17α-hydroxypregnane-20-one series takes place only under very strong conditions, for example, by using an acid anhydride at a boiling temperature and in the presence of a strong acidic catalyst. According to the present invention, this esterification is very much facilitated by the presence of a phosphoric ester group at C-21.

In fact we have quite unexpectedly found that the direct 17-acylation of the 17α-hydroxysteroid-21-phosphates can be carried out under much milder conditions than when at the 21-position, an hydroxyl, an acyl group, a hydrogen or an halogen atom is used in place of the phosphoric acid residue. It is therefore sufficient to carry out the esterification reaction not only by using the acid anhydride alone, i.e., in the absence of any catalyst, but also by using this acid anhydride diluted with a suitable solvent, which may be the acid corresponding to the anhydride itself, or with an aprotic solvent such as dimethylformamide or dimethylsulphoxide, methylene chloride or chloroform, or even acetone.

Furthermore, it is possible to carry out the reaction at room temperature or even lower, and in this case, the time of reaction may be prolonged if necessary.

It is well known to those skilled in the art that, by performing the direct acylation of a normal 17α-hydroxypregnane-20-one, (i.e., without the phosphoric ester group at C-21) in many cases undesired reactions take place. These undesired reactions take place when, in the molecule of the steroid in question, a hydroxy group linked at C-11 with β orientation is present and/or when there is present a $\Delta^4$-3-keto-group. In these cases, under the strong conditions required for the acylation of the 17α-hydroxyl-group, the esterification of the 11β-hydroxyl-group and/or the formation of the enol ester of the $\Delta^4$-3-keto steroid, precede the 17α-hydroxy-group in entering the reaction. On the contrary the mild conditions described above for the acylation of the 17α,21-dihydroxypregnane-20-one-21-phosphates enable one to carry out such acylation without any of the undesired reactions indicated above.

The second step of the process of the present invention, consists of subjecting the intermediate 17-acyl-ester-21-phosphates to the hydrolysing action of an acid phosphatase, under suitable pH conditions, so as to split off the phosphoric acid residue at C-21 without affecting the 17-acyl-group.

It is well known that the phosphatase may be found in all organisms either mono- or poly-cellular ones and in the animal as well as in the vegetable kingdom. They are generally classified as "acid" or "alkaline" phosphatases according to the optimal activity they display in the acid or alkaline range. For the enzymatic hydrolysis of the 21-phosphate 17-esters, due to reasons of economy we chose mainly bacterial, fungal or vegetable phosphatases.

Depending upon the situation, we used cellular suspensions or juices or aqueous extracts recovered from the starting materials. In particular, the aqueous extract of rice bran has proved to be very effective in bringing about the hydrolysis of the 21-phosphates, apart from offering the remarkable advantage of being quite inexpensive.

Rice bran extract, as well as other aqueous extracts or juices obtained from different vegetable tissues, can be prepared extemporaneously to be used as such, without further treatments and/or purifications. It may be convenient, however, to lyophylize the aqueous extract, eventually in the presence of a suitable inert carrier such as mannitol or glycine, or to precipitate the phosphatase enzyme by addition of acetone or ethanol. In this way the phosphatase enzyme is obtained as a powder which may be easily stored for a long time, without any appreciable reduction of the phosphatase activity. If suitably prepared they are less subject to contamination by microorganisms.

In some cases, such as with the juice of squeezed potatoes, precipitation with organic solvents, as well as more sophisticated methods of purification, help to eliminate enzymatic activities different from that useful in the present application and which can affect the yields of the operation.

The aqueous extract of rice bran duly lyophylized, as well as the powder obtained by precipitation with acetone from potato juice, can be used without further purification, with excellent results for the enzymatic dephosphorylation. Of course, in addition to the crude phosphatases, the commercial acid phosphatases can also be used, which are available in a very highly purified form as standards for the determination of the amount of the acid phosphatase present in the blood.

Some commercial products having enzymatic activity, derived for example from *Aspergillus Oryzae* or from *Aspergillus Niger*, prepared for other uses and wherein the phosphatases, even if present, are not the principal enzymes, can also be used with fairly good results. Therefore, the dephosphorylation of the 21-phosphate-17-acyl esters of steroids can be carried out by means of any culture or enzymatic extract with phosphatase activity, as long as it is able to act in acid media and without affecting in any way the steroid molecule or hydrolyzing the 17-acyloxy group.

Since good results with the rice bran extract and with its related lyophylized product were achieved, the invention will here be described and illustrated with particular reference to this means of dephosphorylation.

It is however understood that the working conditions which will be described hereinafter, are only shown in order to illustrate and not to limit in any way the modality and the scope of the present invention.

The enzymatic dephosphorylation was carried out by bringing an aqueous solution of the 21-phosphate-17 acyl ester together with a raw lyophylized extract of rice bran in an acid buffered solution, for example, a buffered solution consisting of acetic acid 0.2M and sodium acetate 0.2M in such proportions to assure an acidity to the reaction mixture at a ph value between 4 and 5. The 21-phosphate can be introduced in the mixture either in free acid or salt form and if necessary adjusting the pH, operating in such a way that the enzymatic hydrolysis takes place in the pH range above mentioned. This not only facilitates the dephosphorylation process, but it does not affect the particular characteristics of the steroid molecule and above all does not cause the transposition of the acyl group from the 17 to the 21-hydroxy-group.

The reaction mixture is allowed to stand for a certain period of time, generally from 6 to 48 hours, in order to enable the enzyme to work entirely.

The hydrolysis can be carried out at a temperature approximately corresponding to the optimum value for the acid phosphatase employed. A preferred range of temperatures is from 10° to 50° C. With the rice bran extract temperatures between 30° and 37° C have proved useful; obviously at lower temperatures the dephosphorylation was slower, while at higher temperatures the process sometimes proceeded more rapidly. If the concentration of the product to be dephosphorylated is sufficiently high, the end product, i.e. the 17-monoester of the 17α,21-dihydroxy steroid, precipitates directly from the incubation mixture, and therefore it may be separated by simple filtration or centrifugation, otherwise it may be extracted with a suitable solvent and purified by subsequent crystallization.

Here it is worthwhile mentioning that it is often possible to avoid isolating the 17-acyloxy-21-phosphate, represented by formula II in the reaction scheme infra. Therefore, the crude aqueous solutions obtained from the acylation reaction and adjusted to a suitable pH, may be used immediately for the enzymatic dephosphorylation.

Obviously this procedure, is often of great advantage from the point of view of working speed as well as the final yield is concerned.

The procedure of 17-acylation and the enzymatic hydrolysis in the 21-position according to the present invention has a wide range of application and it can be used advantageously for the production of a number of 17-monoesters of corticosteroids starting from the corresponding 17α-hydroxy-21-phosphates.

This conversion may be illustrated by the following reaction scheme:

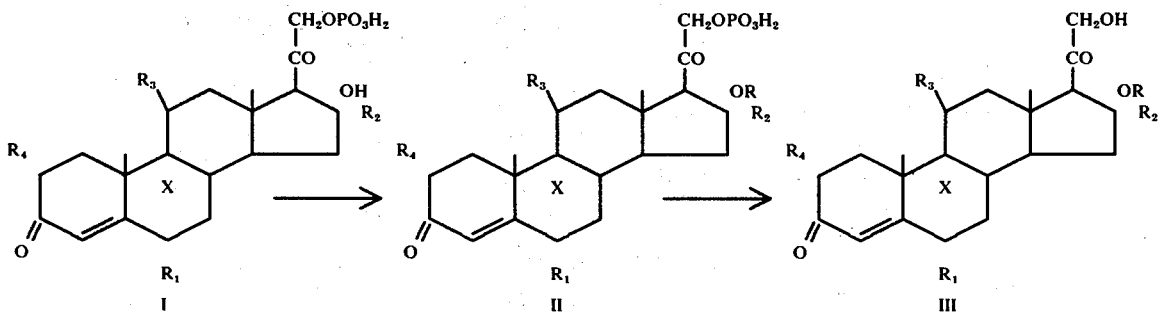

in which the dotted line in ring A indicates a single or double bond in position 1:2;

R is an acyl radical of an aliphatic, cycloaliphatic, aromatic or aryl aliphatic acid containing up to 11 carbon atoms;

R1 is hydrogen, as well as an α- or β-oriented fluorine or chlorine atom, or a methyl or a trifluoromethyl group;

R2 is a hydrogen atom, an α- or β-oriented hydroxy group, preferably esterified or etherified, an α- or β-methyl group, a methylene, a fluoromethylene or chloromethylene group;

R3 is hydrogen or chlorine or fluorine atom or a hydroxyl or keto group,

R4 is hydrogen, fluorine, chlorine, bromine atom, methyl and methylene group, and X is hydrogen, fluorine and chlorine atom.

The following examples are reported to illustrate the invention, but they are not to be construed as limiting.

The new compounds are a series of 17-acyl-esters of 17α,21-dihydroxy-20-keto-steroids of the partial structure:

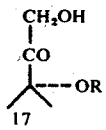

wherein R is an acyl radical of an aliphatic, cycloaliphatic, aromatic or aryl aliphatic acid containing up to 11 carbon atoms inclusive. Particular species thereof are described infra at Example 15.

If desired, the 17-acyl-esters of 17α,21-dihydroxysteroids of the pregnanes series prepared according to the present invention can be further esterified in accordance with well-known procedures to 17,21-diacyl-esters. This further esterification process, which also may be performed without isolating and purifying the 17-monoesters, will give 17,21-diacyl-esters with the acyl residues in the 17 and 21 positions which are the same or different.

EXAMPLE 1

Prednisolone 17-acetate 21-phosphate a. Prednisolone 21-dihydrogenphosphate (5g.) was suspended in 35 ml. of acetic acid and 25 ml. of acetic anhydride and the mixture allowed to react for about 72 hours at a temperature of 4°–5° C.

Then 113.5 ml. of a 0.1N sodium hydroxide solution were added under stirring and cooling and the stirring continued for about 30 minutes. The solution was washed with ethyl ether, using 5 portions of 50 ml. each. The aqueous layer was strongly acidified with 37% hydrochloric acid, salted out with sodium chloride and extracted several times with tetrahydrofuran using about 200 ml. of this solvent.

The combined organic extracts were concentrated in vacuum to a small volume and the concentrate was taken up twice with methanol. After concentration of the solution to about 35 ml., the pH value was adjusted with 1N sodium methoxide to about 7 and the suspension filtered. After further concentration to about 15 ml. and dilution with ethyl ether a product precipitates which, after decantation at 0° C, is filtered and dried. 4G. of sodium salt of prednisolone 17-acetate 21-phosphate was thus obtained, with the following physicochemical characteristics:

$[\alpha]_D^{25°} = 39.4$ ($c = 1\%$, $H_2O$);

$E_{1cm}^{1\%} = 254.2$ in $H_2O$ ($\lambda$max 247m$\mu$ ± 1).

b. To 1 g. of prednisolone 21-dihydrogen phosphate, dissolved in 20 ml. of acetone were added 10 ml. of acetic anhydride with stirring. The reaction mixture was kept at +5° C for 8 days.

Then by external cooling 22.7 ml. of 0.1N sodium hydroxide were added with stirring.

The solution was then concentrated in vacuum to completely eliminate acetone, thereafter the aqueous solution was washed with ethyl ether up to complete removal of acetic acid. By working up the reaction mixture as indicated under a), 0.900 g. of the sodium salt of prednisolone 17-acetate 21-phosphate was obtained.

EXAMPLE 2

Preparation of raw acid phosphatase from rice bran 100 g. of fresh rice bran were suspended in 250 cc. of distilled water and 5 cc. of chloroform. This suspension was left overnight at +2° C, then centrifuged and the supernatant liquid decanted. To this, still opalescent, a filtration aid is added, Clarcel of the firm CECA, and the suspension was stirred and again centrifuged, thus forming a rather limpid supernatant.

This solution may be employed as such.

In order to maintain the phosphatase activity for a long time the solution may be lyophilized.

In the following experiments the lyophilized product of the above solution to which was added 5% (w/v) of mannitol was always used as such for the enzymatic dephosphorylation as described in Example 3.

According to an alternative method, 5% (w/v) of mannitol is added, to the solution obtained after filtration, the whole mixture is concentrated to about half the initial volume and diluted with 10 volumes of acetone. The abundant precipitate thus formed, is filtered and dried under vacuum over anhydrous calcium chloride. It may be used for the dephosphorylation similarly to the lyophilized product.

EXAMPLE 3

Prednisolone 17-acetate from the corresponding 21-phosphate sodium salt 1 g. of prednisolone 17-acetate 21-phosphate sodium salt was dissolved in 7 ml. of 0.2M acetate buffer at pH = 4 ($CH_3COOH$ 0.2M 82 and $CH_3COONa$ 0.2M 18). Separately in 26 ml. of this buffer there are dissolved 4 g of lyophilized raw extract of rice bran, prepared as described above. The turbid solution is centrifuged and the limpid surnatant liquid is added to the solution containing the steroid 21-phosphate.

The reaction mixture is left overnight at 34° ± 2° C: the precipitate formed is filtered on a Buchner funnel and thoroughly washed with water.

After recrystallization from aqueous methanol 0.500 g. of prednisolone 17-acetate was obtained; m.p. 240°–242° C.

EXAMPLE 4

Preparation of prednisone 17-acetate 21-phosphate and conversion to 17-acetate

About 3 g. of prednisone 21-dihydrogen phosphate suspended in 30 ml. of acetic acid and 15 ml. of acetic anhydride are allowed to react under stirring at about 26° C.

After 2–3 hours complete dissolution is observed. The reaction was stopped after 48 hours by adding 68.4 ml. of 0.1N sodium hydroxide under stirring and cooling.

Stirring was continued for about 1 hour, then the solution was washed with ethyl ether using 5 portions of 50 ml. each. The aqueous layer was strongly acidified with 37% hydrochloric acid, 10 g. of sodium chloride was added, after which it was extracted with 3 portions of tetrahydrofuran of 40 ml. each.

The extract was concentrated under vacuum to a small volume, taken up twice with methanol and again concentrated to about 30 ml. The pH value of the concentrate was adjusted to about 7.5 with 1N sodium methoxide. Then the solution was filtered through a paper fluted filter and concentrated to about 15 ml. By the addition of 1 volume of acetone and 10 volumes of ethyl ether a precipitate separated.

The precipitate was filtered, well washed with ether and put in a drying apparatus under vacuum, thus obtaining 3.2 g. of prednisone 17-acetate 21-phosphate sodium salt showing the following physico-chemical characteristics:

$[\alpha]_D^{25°}$ = +85.7° ($c$ = 1%, $H_2O$);
$E_{1cm}^{1\%}$ = 264.3 in $H_2O$ ($\lambda$max = 245 m$\mu$ ± 1).

1 g. of this product is dissolved in 7 ml. of 0.2M acetate buffer at pH = 4. To this solution 4 g. of lyophlized acid phosphatase dissolved in 26 ml. of the same buffer were added.

The solution was allowed to react for 20 hours, then the prednisolone 17-acetate precipitated was filtered from the reaction mixture.

EXAMPLE 5

Conversion of betamethasone 21-dihydrogen phosphate to betamethasone 17-valerate 5 g. of betamethasone 21-dihydrogenphosphate dissolved in 50 ml. of acetone were added to 50 ml. of valeric acid anhydride and allowed to react for 12 days at a temperature of 30° C ± 2° C.

After this time 105.8 ml. of 0.1N sodium hydroxide were added under stirring. Stirring is continued for 15 minutes, then a distillation under vacuum was performed to eliminate acetone. The aqueous solution, turbid because of the presence of the organic reagent, was washed with ethyl ether so as to completely remove said turbidity: the clear solution was acidified with 37% hydrochloric acid and extracted with 3 portions of 100 ml. of ethyl acetate. The combined organic extracts were dried over sodium sulphate, concentrated under vacuum to dryness and taken up with 50 ml. of methanol.

This solution was neutralized with 1N sodium methoxide to a pH of about 7, filtered and concentrated to about 25 ml.

By adding 250 ml. of ethyl ether the crude betamethasone 17-valerate-21-phosphate sodium salt is precipitated. It may be purified by dissolving it in methanol and by subsequent precipitation with ethyl ether. Physico-chemical characteristics:

$[\alpha]_D^{25°}$ = 73.4° ($c$ = 1%, $H_2O$);
$E_{1cm}^{1\%}$ = 240.3 in $H_2O$ ($\lambda$max = 243 m$\mu$ ± 1).

1 g of the compound thus obtained was treated with 3 g. of raw acid phosphatase dissolved in an acetate buffer according to the procedure of Example 3. 630 mg. of betamethasone 17-valerate are obtained; m.p. 181°–184° C.

EXAMPLE 6

Conversion of betamethasone 21-dihydrogen phosphate to betamethasone 17-acetate 1 g. of betamethasone 21-dihydrogen phosphate was dissolved in a mixture consisting of 7 ml. of acetic acid and 5 ml. of acetic anhydride, the reaction mixture was left for 8 days at ±5° C, then 21.1 ml. of a 0.1N sodium hydroxide solution were added under stirring and external cooling. The aqueous solution was then repeatedly washed with a total of 150 ml. of ethyl ether, then worked up as indicated in Example 1 to give 900 mg. of betamethasone 17-acetate-21-phosphate disodium salt. The product thus obtained was dissolved in 30 ml. of distilled water and acidified to a pH of about 1 with 4N hydrochloric acid. After 1 hour stirring and 4 hours decanting at a temperature of 4° to 5° the precipitate was collected by filtration, dried under vacuum obtaining 512 mg. of practically pure betamethasone 17-acetate-21-dihydrogen phosphate having the following physicochemical characteristics:

$[\alpha]_D^{25°}$ = +82.39° ($c$ = 0.5%, methanol);
$E_{1cm}^{1\%}$ = 298 in methanol ($\lambda$max = 241 m$\mu$ ± 1).

On hydrolysing this compound according to the method described in Example 3 it was transformed into betamethasone 17-acetate; m.p. 239°–240° C.

EXAMPLE 7

Compound S 17-acetate 10 g. of Compound S 21-dihydrogen phosphate were suspended in 10 volumes of acetic acid and 5 volumes of acetic anhydride. Compound S is 4-pregnane-17α,21-diol-3,20-dione.

The suspension was stirred at a temperature of about 26° C.

After about 1 hour complete dissolution was observed and after about 24 hours the reaction was practically complete.

234.7 ml. of 0.1N sodium hydroxide were added under stirring and external cooling and then by operating according to the method described in Example 1, 10 g. of the sodium salt of Compound S-17-acetate 21-dihydrogenphosphate were obtained. On hydrolysing this compound according to the method described in Example 3, it is transformed into Compound S-17-acetate.

EXAMPLE 8

Prednisone 17-propionate 1 g. of prednisone 21-dihydrogenphosphate were suspended in 30 ml. of a mixture (1:1) of acetone and propionic anhydride.

The suspension was refluxed for 5 hours, then 23 ml. of 0.1N sodium hydroxide were added. After acetone was distilled off in vacuum, the aqueous solution was washed with ethyl ether to remove the propionic anhydride and the reaction mixture was worked up as indicated in Example 1 yielding 0.750 g. of prednisone 17-propionate 21-dihydrogenphosphate.

By operating practically in the same way prednisone 17-butyrate 21-phosphate and cortisone 17-butyrate 21-phosphate may be obtained.

On hydrolizing these compounds according to the method described in Example 3, they are converted into prednisone 17-propionate, prednisone 17-butyrate and cortisone 17-butyrate respectively.

EXAMPLE 9

Conversion of dexamethasone 21-dihydrogenphosphate to dexamethasone 17-valerate

Dexamethasone 21-dihydrogenphosphate (10g.) was reacted with valeric anhydride according to the method described in Example 5.

Dexamethasone 17-valerate 21-phosphate sodium salt was obtained in an amount of 7 g., showing the following physico-chemical characteristics:

$[\alpha]_D^{25°} = +30.03°$ ($c = 0.5\%$, $H_2O$);

$E_{1cm}^{1\%} = 245.2$ in $H_2O$ ($\lambda$max 243 m$\mu$ ± 1).

This intermediate product treated with a lyophylized extract of rice bran according to the method described in Example 3 forms practically pure dexamethasone 17-valerate at thin-layer chromatography.

EXAMPLE 10

Transformation of betamethasone 21-dihydrogenphosphate to betamethasone 17-acetate without isolating the intermediate product 5 g. of betamethasone 21-dihydrogen phosphate were reacted with acetic anhydride according to the method of Example 6. When the reaction was completed 105.9 g. of 0.1N sodium hydroxide were added and the acetic acid was removed by washing with ether.

The ethyl ether was evaporated off and the aqueous solution buffered to pH 4 with 50 ml. of 0.2M acetate buffer.

To this solution 20 g. of rice bran extract dissolved in 100 ml. of acetate buffer were added. The resulting suspension was centrifuged and the supernatant allowed to react at 34° ± 2° C for 24 hours.

Afterwards the dephosphorylated steroid was extracted with 3 × 150 ml. of chloroform, the combined organic extracts dried over anhydrous sodium sulfate and concentrated under vacuum to dryness. 3.3 g. of betamethasone 17-acetate were obtained which can be recrystallized from methanol 80%.

EXAMPLE 11

Prednisone 17-acetate 21-dihydrogenphosphate

To a suspension of 0.500 of prednisone dihydrogen phosphate in 5 ml. of glacial acetic acid, previously cooled at 15° C were added 2.5 ml. of acetylchloride under stirring.

The reaction mixture was maintained at about 15° C for 24 hours; afterwards 10 ml. of water was added and the pH adjusted to about 5 with 1N sodium hydroxide. Thin-layer chromatography showed that prednisone 17-acetate 21-dihydrogen phosphate was the almost sole reaction product.

EXAMPLE 12

Prednisone 17-formate 21-dihydrogenphosphate

Prednisone 21-dihydrogen phosphate (500 mg.) was dissolved in 10 ml. of formic acid (99%) and allowed to react for 10 days at about 24° C.

Thin-layer chromatography of the reaction mixture, after dephosphorylation by means of lyophylized rice bran extract, showed it to consist of prednisone 17-formate, with traces of the parent 17α-hydroxysteroid.

EXAMPLE 13

6α,9α-Difluoro-16α-methylprednisolone 17-valerate

To a solution of 5 g. of 6α,9α-difluoro-16α-methylprednisolone 21-dihydrogen phosphate in 50 ml. of acetone were added 50 ml. of valeric acid anhydride. The reaction mixture was kept at 30° for 15 days.

Then, under stirring and external cooling 102 ml. of 0.1N sodium hydroxide solution were added.

In order to completely eliminate the acetone, the solution was concentrated under vacuum and then the aqueous solution is washed with ethyl ether so as to completely remove valeric acid and valeric acid anhydride. The aqueous solution was strongly acidified with 37% hydrochloric acid, salted out with sodium chloride and extracted several times with tetrahydrofuran. The combined extracts were concentrated under vacuum to a small volume and then methanol was added. After further concentration of the solution the pH was adjusted to about 7 with 1N methanolic sodium methoxide. The solution was again concentrated and a precipitate was formed by dilution with ethyl ether consisting of 6α,9α-difluoro-16α-methylprednisolone-17-valerate 21-dihydrogen phosphate sodium salt.
Physico-chemical characteristics:
$[\alpha]_D^{25°} = +29.6°$ (1%, water);
$E_{1cm}^{1\%} = 251$ in methanol ($\lambda$max 238–239 m$\mu$).

1 g. of the compound thus obtained, was treated with 3 g. of raw acid phosphatase dissolved in an acetate buffer according to the procedure of the Example 3. 650 mg. of 6α,9α-difluoro-16α-methylprednisolone-17-valerate were obtained.
Physico-chemical characteristics:
$[\alpha]_D^{25°} = +4.4°$ (1%, dioxane);
$E_{1cm}^{1\%} = 319$ (methanol);
1R (cm$^{-1}$): 1730, 1715, 1666, 1625, 1612, 1308, 1260, 1110, 1095, 1070, 1030, 990;
m.p. = 203°–209° C.

EXAMPLE 14

6α,9α-Difluoro-16α-methylprednisolone 17-acetate 1 g. of 6α,9αdifluoro-16α-methylprednisolone 21-dihydrogen phosphate was dissolved in a mixture of 7 ml. of acetic acid and 5 ml. of acetic anhydride. The reaction mixture was allowed to react for 7 days at +5° C, then 20.4 ml. of 0.1N of sodium hydroxide were added under stirring and external cooling.

The aqueous solution was repeatedly washed with a total of 150 ml. of ethyl ether, then it is worked up as in Example 5, to give 900 mg. of 6α,9α-difluoro-16α-methylprednisolone 17-acetate 21-dihydrogen phosphate sodium salt.

On hydrolyzing this compound according to the method described in Example 3, it was converted into 6α,9α-difluoro-16α-methylprednisolone 17-acetate.

EXAMPLE 15

By operating as described in the foregoing examples and by using suitable 17α-hydroxy-corticosteroids 21-phosphates as starting materials the corresponding 17-acyloxy-21-phosphates are obtained by treatment with the anhydride or the acyl chloride of the selected organic acid.

On hydrolysis of these intermediates with acid phosphatases according to the procedures described in the foregoing examples the following 17-monoesters were obtained:

9α-fluoro-16β-methylprednisolone 17-formate;
9α-fluoro-16β-methylprednisolone 17-butyrate;
9α-fluoro-16β-methylprednisolone 17-isobutyrate;
9α-fluoro-16β-methylprednisolone 17-propionate;
9α-fluoro-16β-methylprednisolone 17-isovalerate;
9α-fluoro-16β-methylprednisolone 17-benzoate;
6α-fluoro-16α-methylprednisolone 17-formate;
6α-fluoro-16α-methylprednisolone 17-acetate;
6α-fluoro-16α-methylprednisolone 17-propionate;
6α-fluoro-16α-methylprednisolone 17-butyrate;
6α-fluoro-16α-methylprednisolone 17-isobutyrate;
6α-fluoro-16α-methylprednisolone 17-valerate;
6α-fluoro-16α-methylprednisolone 17-isovalerate;
6α-fluoro-16α-methylprednisolone 17-benzoate;
6α, 9α-difluoro prednisolone 17-propionate;
6α, 9α-difluoro prednisolone 17-butyrate;
6α, 9α-difluoro prednisolone 17-isobutyrate;
6α, 9α-difluoro prednisolone 17-valerate;
hydrocortisone 17-oenantate;
hydrocortisone 17-cyclopentanecarboxylate;
9α, 11β-dichloro 17α, 21-dihydroxy-1, 4-pregnadiene-3, 20-dione 17-propionate;
9α, 11β-dichloro 17α, 21-dihydroxy-1, 4-pregnadiene-3, 20-dione 17-valerate;
9α, 11β-dichloro 16α-methyl-17α, 21-dihydroxy-1, 4-pregnadiene 3, 20-dione 17-propionate;
9α, 11β-dichloro 16α-methyl-17α, 21-dihydroxy-1, 4-pregnadiene 3, 20-dione 17-benzoate;
6α, 9α-difluoro-16α-methylprednisolone 17-propionate;
6α, 9α-difluoro-16α-methylprednisolone 17-butyrate;
6α, 9α-difluoro-16α-methylprednisolone 17-benzoate;
6α-methylprednisolone 17-acetate;
6α-fluoroprednisolone 17-butyrate;
6α-methyl-9α-fluoroprednisolone 17-valerate;
6α-fluoro-9α-chloroprednisolone 17-propionate;
6α-fluoro-9α, 11β-dichloro-17α, 21-dihydroxy-1, 4-pregnadiene 3, 20-dione 17-valerate;
6α, 16α-dimethyl-9α-fluoroprednisolone 17-propionate;
9α-fluoro 16-methyleneprednisolone 17-butyrate;
6α, 9α-difluoro-16-methyleneprednisolone 17-valerate;
6α-trifluoromethylprednisolone 17-butyrate;
6α, 9α-difluoro-16α-fluoromethylprednisolone 17-valerate;
6α, 9α-difluoro-16α-fluoromethylene prednisolone 17-valerate;
16β-methylprednisone 17-formate;
16β-methylprednisone 17-acetate;
16β-methylprednisone 17-valerate;
6α, 9α-dichloro-16β-methylprednisolone 17-formate;
6α, 9α-dichloro-16β-methylprednisolone 17-valerate;
9α-fluorohydrocortisone 17-butyrate;
9α-fluoroprednisolone 17-valerate;
9β, 11β-epoxy-16β-methyl-17α, 21-dihydroxy-1, 4-pregnadiene-3, 20-dione 17-valerate;
9β, 11β-epoxy-6α-fluoro-16α-methyl-17α, 21-dihydroxy-1, 4-pregnadiene-3, 20-dione 17-valerate;
9β, 11β-epoxy-16α-methyl-17α, 21-dihydroxy-1, 4-pregnadiene-3, 20-dione 17-butyrate.

These 17-monoesters are valuable anti-inflammatory steroids similar to betamethasone 17-valerate.

EXAMPLE 16

6α,9α-Difluoroprednisolone 17-butyrate 21-acetate

To a solution of 1.5 g of 6α,9α-difluoroprednisolone 21-dihydrogenphosphate in 30 ml of acetone, 15 ml of butyric anhydride were added at room temperature and the mixture maintained at +28° for 70 hours. Then under stirring and external cooling, 37 ml of 0.1N sodium hydroxide was cautiously added, whereupon the whole mixture was concentrated at a reduced pressure to about 55 ml. The resulting residue was extracted several times with ethyl ether to remove completely unreacted anhydride and free butyric acid. From the aqueous layer ethyl ether was removed by insufflation of nitrogen, after which 15 ml of 0.2M acetate buffer (pH 4) prepared according to Example 3 were added. The water solution thus obtained was treated with 30 ml of the same acetate buffer containing 6 g of lyophilized rice bran extract and maintained at about 35° C for 1 day.

The mixture was then extracted 3 times with chloroform.

The combined chloroform layers were washed with water, dried over anhydrous sodium sulfate and evaporated in vacuum. The solid residue was taken up with 7 ml of pyridine and 2.5 ml of acetic anhydride and maintained at 0° C for 18 hours, afterwards the mixture was treated with ice and water and extracted with methylene chloride. The methylene chloride solution was passed through a chromatographic column on 40 g alumina. After evaporation in vacuum to dryness and recrystallization of the residue from ethanol, 1 g of 6α, 9α-difluoroprednisolone 17-butyrate 21-acetate was obtained.

Melting point 192°–194° C; $[\alpha]_D = +30°$ (dioxane).

EXAMPLE 17

Betamethasone 17,21-dipropionate

Betamethasone 21-dihydrogenphosphate (1 g) was suspended in a mixture of 10 ml of acetone and 5 ml of propionic anhydride and allowed to stand at 25° C for 10 days with occasional stirring. The reaction mixture was then diluted with 21.1 ml of ice-cold 0.1N sodium hydroxide and concentrated under a reduced pressure in order to remove completely acetone. The cloudy solution was repeatedly shaken with ethyl ether and from the now clear aqueous layer, ethyl ether was removed by concentration under vacuum. The pH value was then adjusted to $\approx 1$ with 2N hydrochloric acid, and the oily precipitate thus formed was extracted with ethyl acetate.

The combined organic layers were dried over anhydrous sodium sulfate and concentrated to a small volume under vacuum, 40 ml. of methanol were added, the solution concentrated in vacuum to about 10 ml and neutralized to pH = 7 with 1N sodium methoxide in methanol. After filtration, concentration to about 3 ml and dilution with 30 ml of ether the precipitate of betamethasone 17-propionate 21-dihydrogenphosphate sodium salt was filtered and dried in vacuum.

To a solution of 1 g of crude betamethasone 17-propionate 21-dihydrogenphosphate sodium salt, obtained as described above, in 20 ml of distilled water, a centrifugal clear solution of 5 g of lyophilized rice bran extract in 30 ml of acetate buffer at pH = 4 were added.

The solution was allowed to stand at 37° C for 40 hours, then the dephosphorilated steroid is extracted with three portions of chloroform. The collected organic layers are dried over anhydrous sodium sulfate, evaporated to dryness in vacuum and the residue was taken up with 6 ml of pyridine and 1 ml of propionic anhydride. The mixture was allowed to stand overnight at 0° C, then poured into ice water. The precipitate was collected and dried under vacuum. After column chromatography on silica gel (70 g) and recrystallization of the residue from acetone-ether, 0.6 g betamethasone 17,21-dipropionate were obtained.

What we claim is:

1. A process for the preparation of 17-monoesters of 17α, 21 dihydroxy steroids comprising:
    esterifying the corresponding 17α, 21-dihydroxy steroid 21-phosphate with an acylating agent to directly and solely esterify the 17α-hydroxy group, and
    then dephosphorylating the intermediate compound 17-acyloxy-21-phosphate by means of enzymatic hydrolysis carried out with an acid phosphatase at a pH in a range which allows sufficient stability of the desired 17-monoester of 17α,21-dihydroxy steroids, and at temperatures about room temperature.

2. The process of claim 1 wherein said acylating agent is an anhydride or chloride of an organic aliphatic, cycloaliphatic, aromatic or arylaliphatic acid containing up to 11 carbon atoms.

3. The process of claim 2 wherein said acylating agent is admixed with a diluent which is the acid corresponding to the acid anhydride or chloride used.

4. The process of claim 2 wherein said acylating agent is admixed with a diluent which is an aprotic solvent selected from the group consisting of acetone, dimethylsulfoxide, dimethylformamide, methylene chloride, chloroform and mixture thereof.

5. The process of claim 2 wherein said acylating agent is admixed with acetone as a diluent.

6. The process of claim 1 in which said acid phosphatase is used in the form of an aqueous suspension or dispersion of cells or tissues or their fragments.

7. The process of claim 6 in which said aqueous suspension or dispersion is prepared from an aqueous extract of tissue that has been filtered and dried.

8. The process of claim 6 in which said aqueous suspension or dispersion is prepared from an aqueous extract of tissue that has been filtered and lyophilized.

9. The process of claim 7 in which said aqueous suspension or dispersion is prepared from an aqueous extract of tissue that has been dried in admixture with an inert carrier selected from the group consisting of mannitol, glycine and mixtures thereof.

10. The process of claim 6 in which said aqueous suspension or dispersion is prepared from an aqueous extract of tissue that has been centrifuged and dried.

11. The process of claim 6 in which said aqueous suspension or dispersion is prepared from an aqueous extract of tissue that has been centrifuged and lyophilized.

12. The process of claim 10 in which said aqueous suspension or dispersion is prepared from an aqueous extract of tissue that has been dried in admixture with an inert carrier selected from the group consisting of mannitol, glycine and mixtures thereof.

13. The process of claim 6 in which an aqueous extract of rice bran is used as source of acid phosphatase.

14. The process of claim 1 in which said intermediate compound 17-acyloxy-21-phosphate is adjusted to a pH between 4 and 5 and maintaining the pH value during the course of said enzymatic hydrolysis.

15. The process of claim 1 wherein the enzymatic dephosphorylation is carried out at a temperature between 10° and 50° C.

16. The process of claim 1 wherein the enzymatic dephosphorylation is performed directly on the reaction mixture of said 17α, 21-dihydroxy steroid 21-phosphate and said acylating agent without isolating the intermediate 17-acyloxy-21-phosphate.

\* \* \* \* \*